United States Patent [19]

Servas et al.

[11] Patent Number: 4,559,999
[45] Date of Patent: Dec. 24, 1985

[54] HEAT EXCHANGER FOR EXTRACORPOREAL CIRCUIT

[75] Inventors: Frank Servas, San Juan Capistrano; John E. Lewin, Santa Ana; Tudor Pavlov, Laguna Niguel; Lambert J. Diettrich, Jr., Leucadia, all of Calif.

[73] Assignee: Shiley, Inc., Irvine, Calif.

[21] Appl. No.: 483,377

[22] Filed: Apr. 8, 1983

[51] Int. Cl.[4] ............................................. F28D 7/12
[52] U.S. Cl. ........................................ 165/156; 165/160; 165/163; 165/164; 165/179; 165/184; 422/46
[58] Field of Search ............... 165/156, 157, 160, 163, 165/164, 170, 179, 184; 422/45, 46, 48

[56] References Cited

U.S. PATENT DOCUMENTS

| 1,453,220 | 4/1923 | Witzenmann | 165/156 |
|---|---|---|---|
| 2,611,585 | 9/1952 | Boling | 165/179 |
| 2,913,009 | 11/1959 | Kuthe | 138/38 |
| 3,249,154 | 5/1966 | Legrand | 165/164 |
| 3,370,153 | 2/1968 | Du Fresne | |
| 3,730,229 | 5/1973 | D'Onofrio | 165/156 |
| 3,731,731 | 5/1973 | Kyvsgnard et al. | 165/46 |
| 3,802,499 | 4/1974 | Garcea | 165/163 |
| 3,882,024 | 5/1975 | Holmes | |
| 4,061,470 | 12/1977 | Leonard | 422/48 |
| 4,138,464 | 2/1979 | Lewin | 165/133 |
| 4,161,214 | 7/1979 | Wendel | 165/179 |
| 4,182,739 | 1/1980 | Curtis | 422/47 |
| 4,187,846 | 2/1980 | Lolachi et al. | |
| 4,231,425 | 11/1980 | Engstrom | 165/156 |
| 4,306,018 | 12/1981 | Kirkpatrick | 422/48 |
| 4,317,268 | 3/1982 | Bowden et al. | 165/163 |
| 4,321,963 | 3/1982 | Bowden | 165/163 |
| 4,347,894 | 9/1982 | Gerlach | 165/163 |
| 4,428,403 | 1/1984 | Lee et al. | 165/156 |
| 4,442,799 | 4/1984 | Craig et al. | 165/163 |
| 4,451,960 | 6/1984 | Meliter | 165/165 |
| 4,466,567 | 8/1984 | Garrison | |

FOREIGN PATENT DOCUMENTS

| 248081 | 8/1961 | Australia | |
|---|---|---|---|
| 492700 | 8/1975 | Australia | |
| 529453 | 12/1978 | Australia | |
| 240584 | 5/1980 | Australia | |
| 62555 | 9/1980 | Australia | |
| 168097 | 12/1981 | Japan | 165/156 |
| 160795 | 9/1983 | Japan | 165/156 |

Primary Examiner—Albert J. Makay
Assistant Examiner—Steven E. Warner
Attorney, Agent, or Firm—Knobbe, Martens, Olson & Bear

[57] ABSTRACT

The oxygenater heat exchanger disclosed utilizes a heat transfer tube having several tube legs arranged in closely spaced, parallel relation. A resilient central core fits resiliently within the tube legs and cooperates with spiral ribs on the tube and with the housing to form blood flow spiral passages down around the exterior of each of the tube legs. The blood inlet is positioned to enhance efficient heat exchange.

15 Claims, 11 Drawing Figures

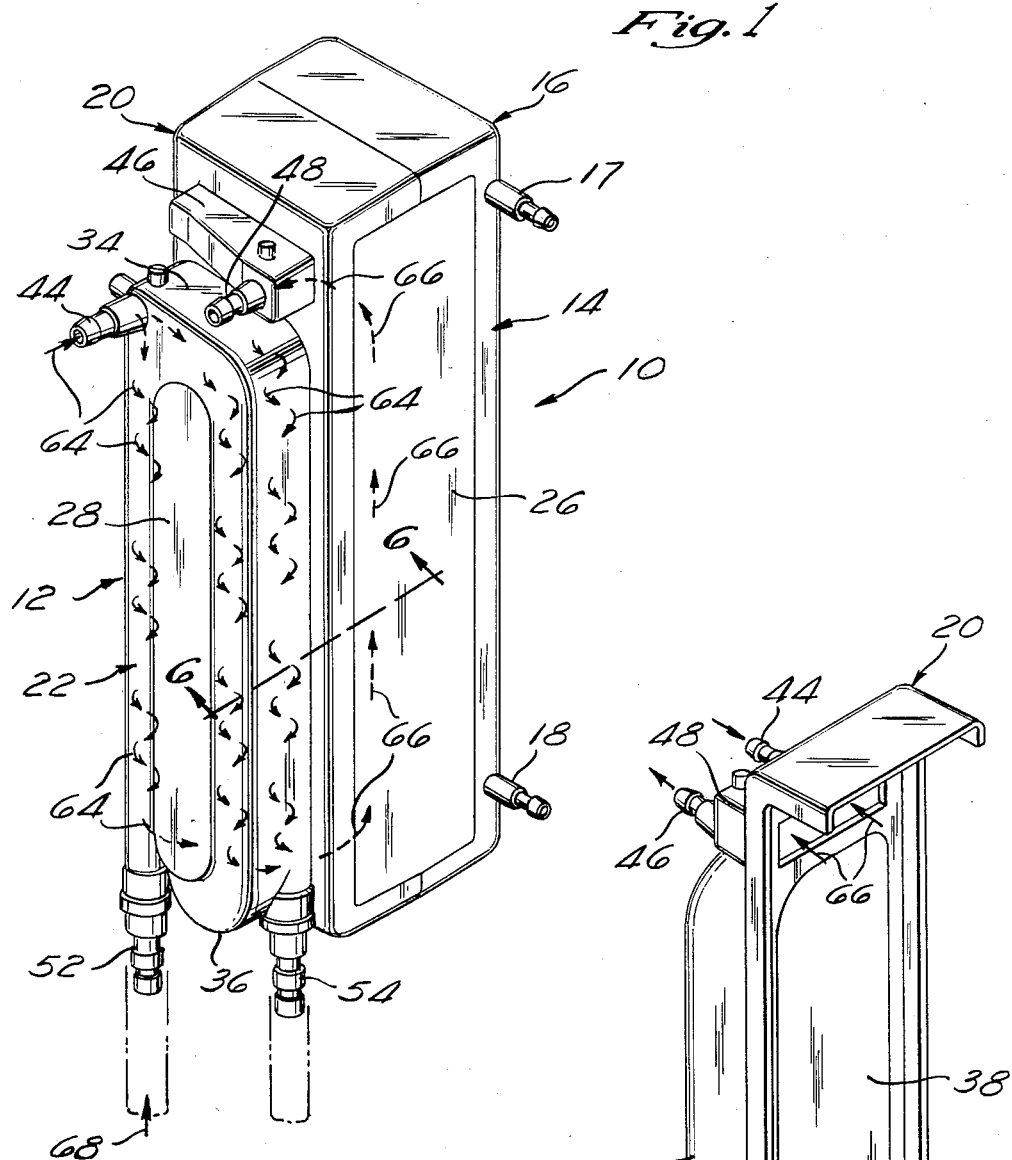

U.S. Patent   Dec. 24, 1985   Sheet 3 of 4   4,559,999
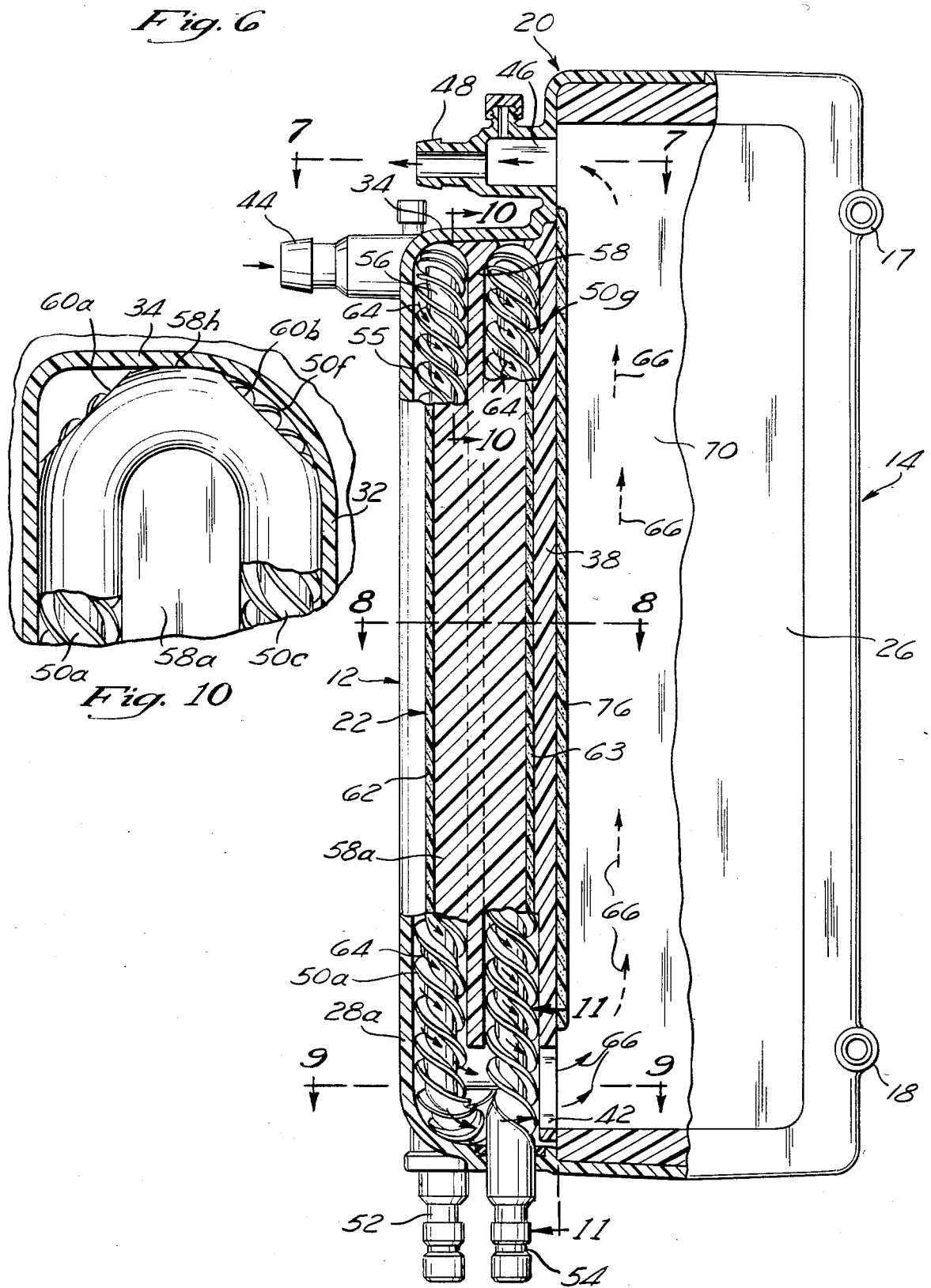

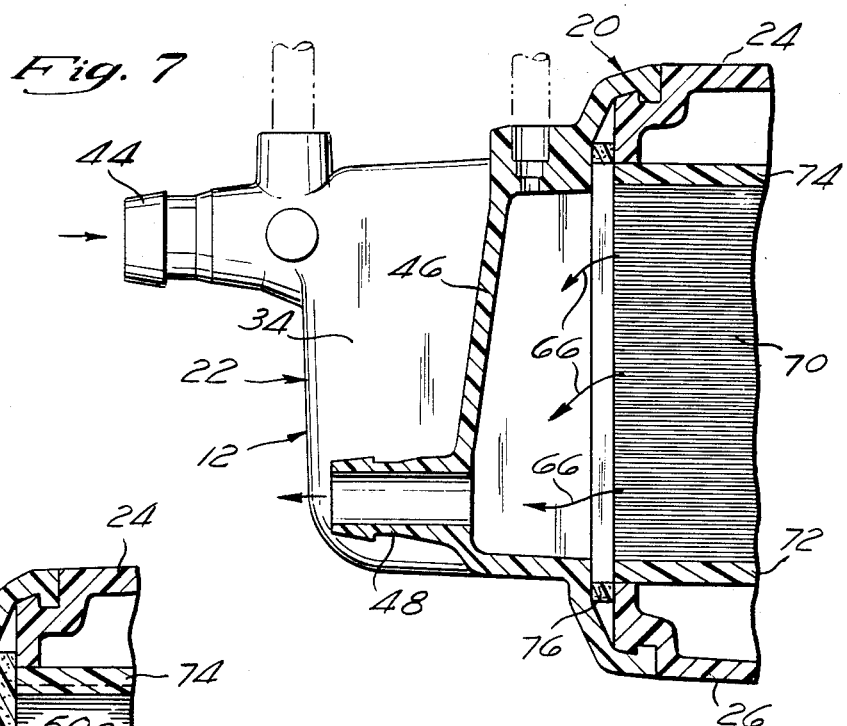
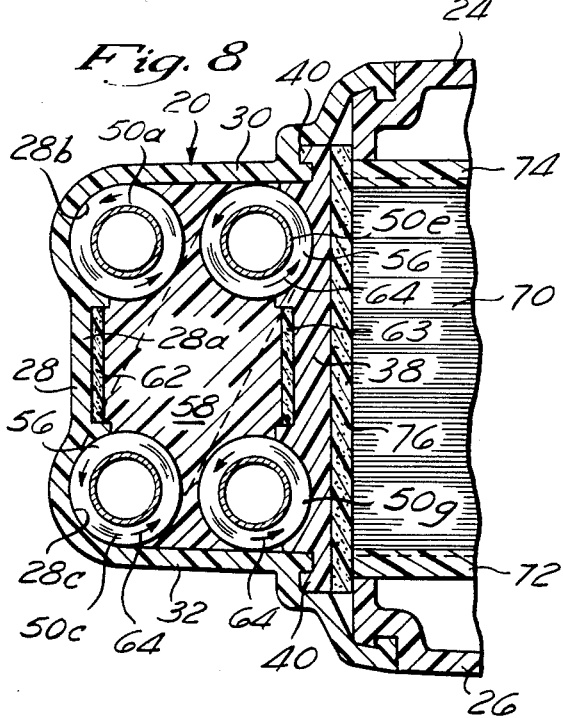
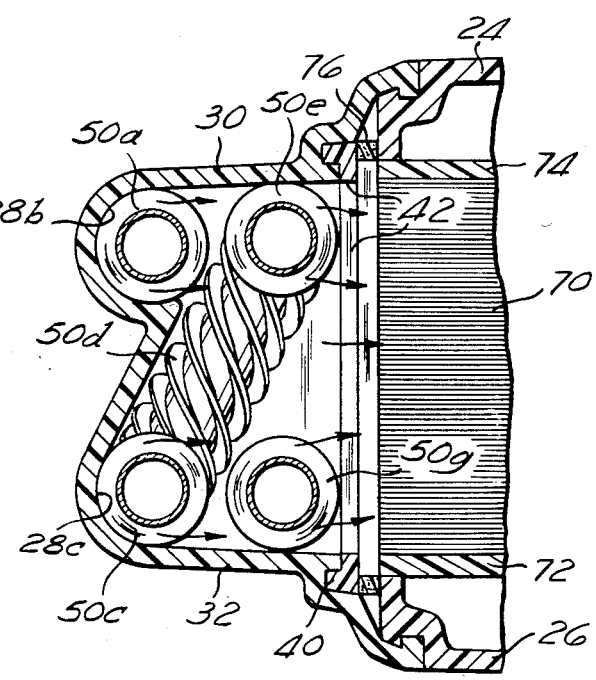
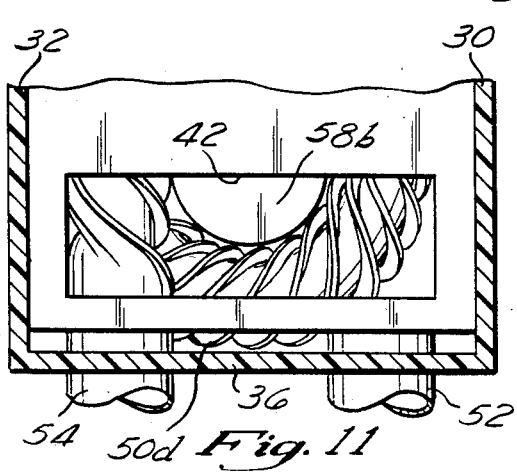

HEAT EXCHANGER FOR EXTRACORPOREAL CIRCUIT

BACKGROUND OF THE INVENTION

This invention relates generally to heat exchangers and more particularly a new heat exchanger for use in an extracorporeal fluid handling system, such as a blood oxygenator or the like.

Circulating blood outside of a person's body has been a routine procedure in the operating room for several years. An important component of such a circuit is a heat exchanger used to lower the temperature of the blood prior to and during a surgical procedure and subsequently rewarm the blood to normal body temperature. The cooled blood induces a hypothermia which substantially lowers the oxygen consumption of the patient. This helps protect the body's vital organs during operative procedures which require interrupting or decreasing the circulation of blood.

A number of different structural configurations for heat exchangers have been used in the extracorporeal blood circuit including hollow metal coils, cylinders and plates through which the heat transfer fluid is circulated. U.S. Pat. No. 4,065,264 discloses a heat exchanger employing spiral tubing having spiral exterior heat exchange ribs which form in combination with a surrounding housing a spiral heat exchange passage for the blood while the heat transfer fluid flows through the tubing. This arrangement provides a very efficient transfer of heat from the blood to the transferred fluid, which is of substantial importance, since the quicker the patient's blood is cooled and rewarmed, the shorter the time the patient has to be connected to the bypass blood circuit. Nevertheless, a continual need exists for improvements in efficiency and overall performance of heat exchangers, as well as manufacturing advantages and costs.

SUMMARY OF THE INVENTION

Briefly stated, the blood oxygenator heat exchanger of the invention includes a plurality of heat exchange tubes positioned in closely spaced relation and preferably interconnected to form a single tube confined within a housing. The exterior of the tubes are formed with outwardly extending ribs, preferably in the form of one or more continuous spirals that extend from one end of the tube to the other. An elastomeric central core fits between and conforms to the tubes to space the tubes and resiliently urge them against the housing, which also conforms to the exterior of the tube ribs. With this arrangement, blood circulation passages are formed by the ribs in combination with the housing and the central core that confine and direct the flow of blood through the heat exchanger and keep the blood in excellent heat exchange relation with the heat transfer ribs. The resilient central core maximizes this confinement without introducing undue stresses on the tubes or the housing.

In a preferred form of the heat exchanger, the inlet and outlet end of the heat exchange tube is at the lower end of the housing and the tube is formed into four elongated legs that extend substantially parallel to each other and are joined by curved sections at their sequential ends. The central resilient core fits between the four legs of the continuous tube and resiliently urges them outwardly against a surrounding housing. The blood enters the housing at the upper end and flows downwardly through spiral passages on the exterior of the heat exchange tube legs and exits from the housing at the lower end of these tube legs.

The blood inlet is preferably located adjacent the upper end of the first leg of the heat exchanger tube so that at low flow rates, most of the blood flows through the passages around the first leg and a third leg that is directly open to the upper end of the first leg. With increased flow rates, the blood flows more evenly through the passages around all four of the legs.

While the blood flows downwardly in the spiral passages, the heat exchange fluid, usually water, flows up and down through the continuous heat exchange tube. Thus, water flows upwardly in the opposite direction from the blood in two of the tube legs and downwardly in the direction of the blood in the other two legs. Maximum heat transfer is obtained with the water flowing contra to the blood. To maximize this effect, the tube legs having the contra flow receive the greater blood flow on their exterior. This is most significant for the first leg since that leg also has the greatest temperature differential being closest to the water inlet.

BRIEF DESCRIPTION OF THE DRAWINGS

FIG. 1 is a perspective view of the exterior of the heat exchanger of the invention shown as an integral portion of a membrane blood oxygenator, including a schematic illustration of the blood and heat exchange fluid flow.

FIG. 2 is a perspective view of the heat exchanger of FIG. 1 by itself as viewed from the blood oxygenator side of the assembly.

FIG. 6 is a cross sectional view of the heat exchanger and blood oxygenator along line 6—6 of FIG. 1.

FIG. 7 is a cross sectional view of the heat exchanger on line 7—7 of FIG. 6 illustrating the blood inlet and outlet.

FIG. 8 is a cross sectional view on line 8—8 of line 6.

FIG. 9 is a cross sectional view on line 9—9 of FIG. 6 showing the heat exchange construction near the blood outlet.

FIG. 10 is a cross sectional view on line 10—10 of FIG. 6 showing the blood inlet construction.

FIG. 11 is a cross sectional view on line 11—11 of FIG. 6 further showing the blood outlet and the lower end of the heat exchange tube.

DETAILED DESCRIPTION OF A PREFERRED EMBODIMENT OF THE INVENTION

Figure 3:
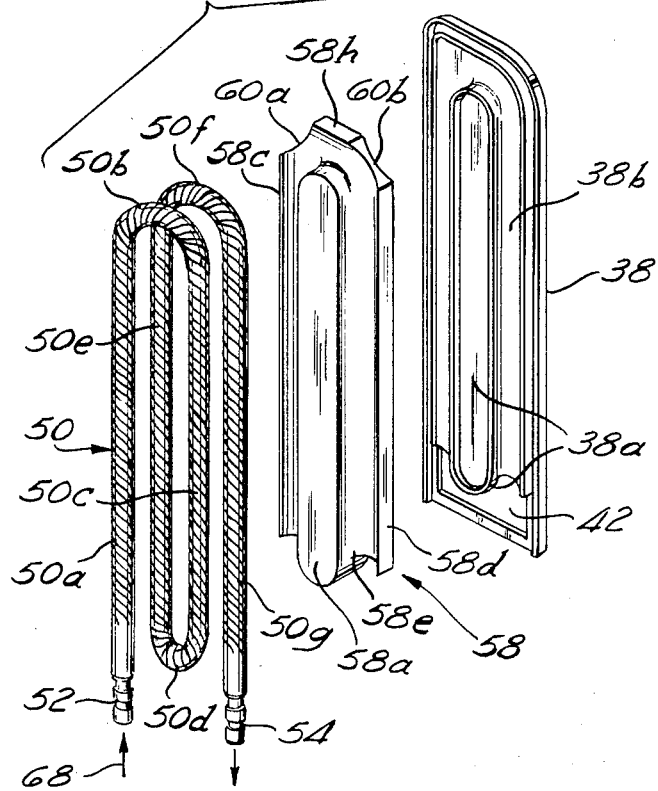
FIG. 3 is a perspective view of the heat exchange tube, the central core, and a portion of the housing, as viewed from a perspective similar to that of FIG. 1.

Referring first to FIG. 1, there is shown a disposable assembly of a blood membrane oxygenator 10 and integral heat exchanger 12. This assembly is adapted to be incorporated in an extracorporeal blood circuit in a vertical orientation as shown in FIG. 1. Oxygenator 10 includes a housing 14 in the general shape of a rectangular prism. The rear wall of the housing 14, as well as approximately half of the top and bottom walls of the housing, are formed by a gas manifold plate 16 having a treating gas inlet 17 and a treating gas outlet 18. The forward half of the top wall and the bottom wall are formed as part of a shell-like blood manifold plate 20 and which forms a portion of the front wall of the housing 14 and also forms the primary component of a heat exchanger housing 22. The oxygenator housing 14 further includes side walls 24 and 26 which cooperate with the gas manifold plate 16 and the blood manifold plate 20.

The heat exchanger housing 22 has a generally oblong shape with the elongated dimension extending vertically as viewed in FIG. 1. The housing 22 includes a front wall 28, side walls 30 and 32, a top wall 34, and a bottom wall 36. As seen from FIG. 2, the rear wall of the heat exchanger housing 22 and a portion of the front wall of the oxygenator housing 14 is formed by a retainer plate 38. As seen from FIG. 8, the plate 38 has a rib and groove connection 40 on each vertical edge that mates with the blood manifold plate 20 in the area of the edges or corners of the heat exchanger housing side walls 30 and 32.

As seen from FIG. 2, a rectangular opening in the lower portion of the retainer plate forms a blood outlet 42 from the heat exchanger housing 22 and a blood inlet to the oxygenator housing 14. In accordance with the invention, a blood inlet 44 extends outwardly from the upper left corner of the front wall 28 of the heat exchanger housing as viewed in FIG. 1. Also formed on the blood manifold plate 20 is a blood outlet manifold 46 which is seen in FIG. 7 open to the upper end of the oxygenator housing interior and leading to a blood outlet tube 48.

As seen in FIGS. 6 and 8, there is positioned within the oxygenator housing 14 a mass of pleated, selectively permeable membrane 70 in rectangular folds parallel to the housing side walls 24 and 26 and sandwiched between slim plates 72 and 74. The membrane is further bounded by a front shunt block 76 and a similar rear block (not shown). One suitable example of blood oxygenator membrane is made of micropourous polypropylene material sold by Celanese Corporation of New York, N.Y., under trade name Celgard. Further details of the construction and operation of the oxygenator are disclosed in a copending, commonly assigned U.S. patent application Ser. No. 473,508, filed Mar. 9, 1983, entited "Membrane Oxygenator".

Figure 4:
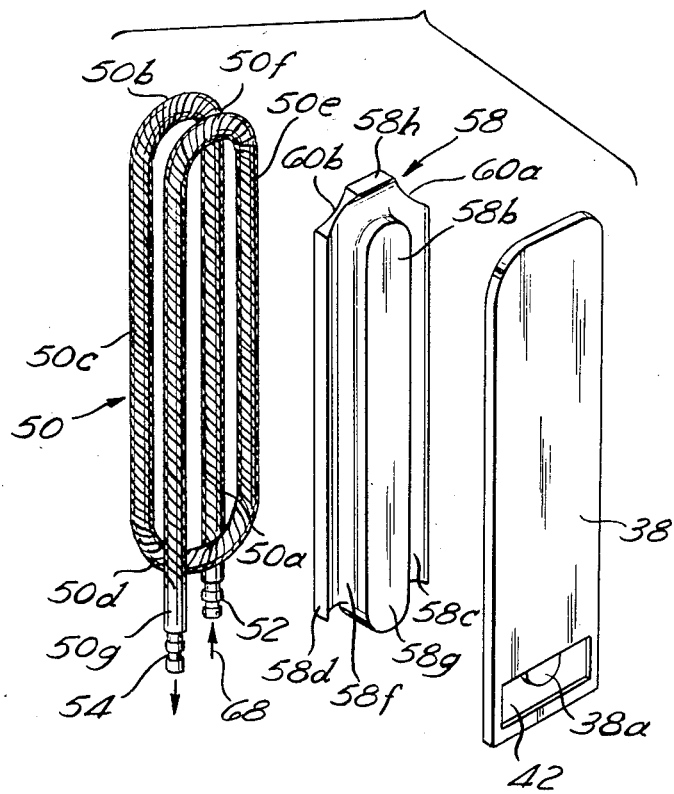
FIG. 4 is a perspective view of the components of FIG. 3 but taken from the angle of FIG. 2.

Referring now to FIGS. 3 and 4, the interior components of the heat exchanger of the invention may be seen to include a continuous tube 50 for ducting water or other suitable heat exchange liquid through the device. The tube 50 includes an inlet end 52 and an outlet end 54, both of which extend through the suitable seals in lower wall 36 of the housing 22. The tube is sinuously formed so as to provide a plurality of elongated, spaced, parallel, vertically oriented tubes or tube portions joined at the upper and lower ends by interconnecting curved portions. More specifically, a first tube leg 50a extends upwardly from the inlet 52 and is connected at its upper end by a smoothly curved upper section 50b to a second vertical leg 50c. The lower end of the leg 50c is connected by a lower curved section 50d which, in turn, is connected to the lower end of a third vertically extending leg 50e, and the upper end of the leg 50e is connected by an upper curved section 50f to the upper end of a fourth leg 50g leading to the outlet 54. The legs 50a and 50c with the curved portion 50b form a U-shaped loop while the legs 50e and 50g together with their connecting curved portion 50e form a second U-shaped loop, and the two U-shaped loops are joined by the lower curved section 50d which extends diagonally between the U-shaped loops.

Figure 5:
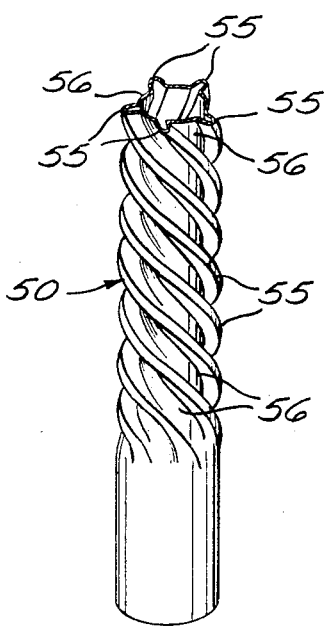
FIG. 5 is a fragmentary perspective view of the heat exchange tube.

The tube 50 is formed in its exterior surface with a plurality of high lead spiral ribs 55 that extend from the inlet end to the outlet end. As best seen from FIG. 5, the ribs are hollow, opening into the interior of the tube to improve heat transfer. Further, it should be noted from the upper end of the portion of the tube shown in FIG. 5, there are five separate high lead ribs, and there are correspondingly five grooves or passages 56 between them.

The tube 50 is preferably made of aluminum which is anodized on its exterior and has several desirable properties for the function to be performed. The exterior anodized material has the necessary compatibility with blood. Aluminum material is a good heat conductor and it is sufficiently ductile that it can be formed in a continuous length or a coil and bent into the configuration illustrated with a suitable cross section. Further details regarding the construction and fabrication of such a tube may be found in U.S. Pat. No. 4,138,464, U.S. Pat. No. Re. 24,783, and U.S. Pat. No. 3,015,355.

Positioned between the tube legs, as shown in FIGS. 6 and 8, but shown in exploded form in FIGS. 3 and 4, is a central core 58 made of a resilient elastomeric material which is compatible with blood. One suitable thermoplastic rubber is a product sold by Shell under the tradename Krayton. The core has a solid, somewhat cross-shaped cross section and includes a front wall segment 58a which has an elongated racetrack shape and extends between the tube legs 50a and 50c, a similar rear wall segment 58b which extends between the tube legs 50e and 50g, a thinner side wall segment 58c which extends between the tube legs 50a and 50e, and an opposite side wall segment 58d which extends between the tube legs 50c and 50g. On the front side of the core, the segment 58a forms the central portion of a U-shaped channel 58e having a configuration that conforms to the U-shaped tube loop 50a, 50b and 50c. Similarly, the segment 58b on the backside of the core 58 is in the center of a U-shaped channel 58f which conforms to the tube U-shaped loop 50e, 50f and 50g. The lower curved end 58g of the core fits within the diagonal, curved tube section 50d.

As seen from FIGS. 6 and 8, the tube 50 with the core 58 centrally positioned within the tube legs snuggly fits within the heat exchange housing 22. The core segment 58a cooperates with a similarly shaped surface 28a on the backside of the front housing wall 28, as may be visualized from FIGS. 1 and 8. In addition, an adhesive-like filler or potting material 62, such as a polyurethane, extends between the segment 58a and the housing wall 28a between the tube legs 50a and 50c. This material seals the connection between the housing wall 28a and the core segment 58a to present blood seepage in that area.

The backside of the front housing wall 28 further includes vertically extending curved wall surfaces 28c and 28b which form part of a U-shaped channel that mates with the tube loop 50a, 50b and 50c. Similarly, the rear core segment 58b mates with the central portion 38a of the retainer wall 38. The portion 38a defines a U-shaped channel 38b which is curved to conform to the shape of the U-shaped loop 50e, 50f and 50g. Again, a suitable potting material 63 extends between the core rear segment 58b and the retainer wall portion 38a.

As also seen from FIG. 8, the core side wall segments 58c and 58d fit snuggly against the inner surfaces of the side walls 32 and 30. Similarly, the upper end 58h of the central core engages the inner surface of the upper housing wall 34, as seen in FIG. 6.

With this snug fitting, resilient relation between the tube legs, the central core, and the surrounding housing, the core and the housing close the passages formed between the spiral ribs 55. Thus, blood entering at the upper end of the heat exchange housing will flow spirally through these passages rather than simply flowing straight downwardly. The lower end of the central core 58 terminates where it engages the lower curved tube section 50d so that the lower sides of the tube exterior passages 56 are all open to the blood outlet 42 in the retainer plate 38, as seen in FIGS. 9 and 11.

However, as seen from FIGS. 3 and 4, the upper corners of the core segments 58c and 58d are not curved to conform to the upper side wall corners of the housing 22. Consequently, the recesses 60a and 60b formed at these core corners form blood flow paths between the upper ends of the exterior of the two U-shaped tube loops. Note from FIGS. 1 and 10 that the recess 60a is directly in the path of the blood inlet 44.

OPERATION

In operation, blood from the patient enters the inlet 44 after the system has been properly primed with a suitable saline solution which removes all air in the blood flow path. The blood flows through the spiral passages 56 of the heat exchanger tube legs, as shown by the arrows 64, and exits from those passages at the lower end of the housing 22, and then flows through the blood outlet 42 leading into the membrane-filled oxygenator housing 14. The flow through the oxygen providing membrane is schematically as indicated by the arrows 66, upwardly through the oxygenator and out through the outlet manifold 46 and the outlet tube 48, as seen in FIGS. 6 and 7.

Considering the blood flow through the heat exchanger housing in greater detail, it will be recognized that the flow is really through the passages 56 surrounding each of the four tube legs 50a, 50b, 50c and 50d. Further, since there are five separate ribs 55 forming five separate passages 56 for each leg, there are a total of twenty separate parallel passages 56 through which blood may flow in heat exchange relation with the tube ribs.

It should be noted, however, that the paths to these passages is somewhat different at the inlet for the four tube legs. Referring to FIGS. 1 and 10, blood entering the blood inlet 44 is first exposed to the upper end of the tube leg 50a such that the path of least resistance is through the passages around the tube leg 50a. Secondly, the recess 60a, in the upper left corner of the core enables blood to flow to the passages surrounding the tube leg 50e. This path, being only slightly longer than the path around leg 50a, has slightly more resistance to flow. However, to flow into the tube leg 50c, the blood must flow through the spiral passages on the curved tube section 50b. Upon reaching the upper end of the tube leg 50c, blood can then also flow through the recess 60b at the upper end of the core to the tube leg 50g. Of course, blood can also reach the leg 50a by way of the curved section 50f through the recess 60a.

Thus, with this strategic inlet arrangement, the blood flows through the tubes selectively as a function of blood flow rate. With a low blood flow rate, a significantly higher percentage of the blood may flow through the passages surrounding the tube legs 50a and 50e than through the other two, but with an increased flow rate the blood distribution switches to be more even through the four legs.

A primary advantage of the blood inlet arrangement relates to the direction of flow of the heat exchange water through the tube 50 and the direction of blood flow through the exchanger. As indicated by the arrows 68 in FIGS. 1, 3 4, the water flows upwardly through the tube leg 50a, downwardly through the leg 50c, upwardly through the leg 50e, and downwardly through the leg 50g to the outlet 54. Thus, the upward direction of flow in leg 50a and 50e is contra to the direction of blood flow around and down the exterior of those legs. Since the amount of water passing upwardly through the tube legs in heat exchange relation with the blood flow is much greater than with downward water flow, the amount of heat exchanged by the contra flow tube legs 50a and 50e is greater than with legs 50c and 50g. Arranging the inlet so that more blood flow around these contra-flow legs than around the same-direction-flow legs 50c and 50g maximizes this effect. Thus, with low flow rates it has been found that the heat transfer efficiency is much better with the inlet as potioned than if it was, say, centrally located. With greater flow, the effect is less significant but nevertheless helpful. Since the temperature differential between the blood and the water is greatest when the incoming water flows adjacent the incoming blood, the heat transfer capacity of tube leg 50a is further enhanced.

A primary advantage of the heat exchanger of the invention is that the core resilienty engages the heat exchange tube and the surrounding housing, and further resiliently urges the heat exchange tube against the housing. This minimizes blood flow directly downwardly through the housing and instead directs substantially all of the blood flow through the spiral passages, and thus maximize heat transfer. At the same time, the resiliency of the arrangement reduces stress on the housing. This permits the housing to be made of injection molded plastic parts, preferably made of a transparent thermoplastic material, such as a polycarbonate, and the gluing of such components together. Non-resilient connection urging the aluminum tube 50 against the plastic housing might result in cracking of the housing.

The efficiency of heat transfer from the blood to the heat transfer fluid is of substantial importance since the quicker the patient's blood is cooled and rewarmed, the shorter the time the patient has to be connected to the bypass extracorporeal blood circuit. The efficiency of a heat exchanger is normally expressed by a performance factor P/F which is the difference in temperature from the blood out and the blood in divided by the difference from the temperature of the coolant in and the temperature of the blood in. Tests conducted on a prototype of the device for bovine blood adjusted to simulate the viscosity of human blood indicate a performance factor of 0.63 and 0.64 for a blood flow rate of 2 liters per minute; 0.486 to 0.516 for a blood flow rate of 4 liters per minute; and 0.394 to 0.447 for a blood flow rate of 6 liters per minute. Based on these initial results, the device appears to provide equivalent performance factors as that of a bubbler oxygenator heat exchanger currently being offered by the assignee of the present invention, but with a smaller package.

What is claimed is:

1. A heat exchanger for regulating the temperature of blood flowing in an extracorporeal blood circuit comprising:

a plurality of closely spaced heat exchange tubes for conducting a heat exchange fluid, outwardly extending rib means formed along the length of each of said tubes;

a housing enclosing the tubes with a heat exchange fluid inlet and a heat exchange fluid outlet extending into and out of said housing, said housing further having a blood inlet and a blood outlet; and a flexible core positioned between the heat exchange tubes and resiliently urging the tubes against the housing and shaped to form, in combination with the housing and said rib means, passages through which blood may flow in heat exchange relation with the heat exchange fluid in the tubes, the resiliency and shape of the core being such that substantially all the blood is directed through said passages to maximize the heat transfer capability.

2. The heat exchanger of claim 1 wherein said rib means are in the form of one or more spiral ribs on each of said tubes so that said passages have a spiral configuration.

3. The heat exchanger of claim 1 or 2 wherein said tubes include substantially elongated portions that extend generally parallel to each other.

4. The heat exchanger of claim 1 wherein said plurality of tubes are connected together to form a single, continuous sinuous tube and said rib means are continuous on said continuous tube to form one or more substantially continuous passages.

5. The heat exchanger of claim 4 wherein said plurality of tubes include four elongated tubular legs joined to form a single continuous tube.

6. The heat exchanger of claim 1 or 5 wherein said core and said housing each include curved portions to conform to the exterior of said rib means, and said core and said housing include interengaging portions which resiliently space the plurality of tubes from each other.

7. The heat exchanger of claim 4 wherein said core has a solid generally cross-shaped cross section including a segment extending between each adjacent pair of tubular legs towards the adjacent housing wall.

8. The heat exchanger of claim 7 wherein the lower end of said core is spaced from the lower end of the housing such that the blood passages on the lower exterior ends of said legs open into a blood outlet for said housing.

9. The heat exchanger of claim 5 wherein said legs are vertically oriented in generally parallel relation and are interconnected by curved portions to form said continuous tube, said blood inlet is located at an upper end of said housing opening onto an upper end of one of said legs, and said inlet to said continuous tube is connected to a lower end of said one of said legs so that heat exchange fluid flow through said one leg is opposite to downward flow of the blood on an exterior surface of said one leg.

10. The heat exchanger of claim 9 including a recess in the upper end of said core allowing blood flow from the upper end of said one of said legs to the upper end of additional tube legs.

11. A heat exchanger for regulating the temperature of blood flowing in an extracorporeal circuit comprising:

a generally elongated housing having an inlet and an outlet for circulating blood therethrough;

a continuous heat exchange tube positioned within said housing having an inlet end and an outlet end extending out of the housing, said continuous tube further including a first elongated leg extending from said inlet and a second elongated leg extending parallel to said first leg and joined to the first leg by a curved section to form a first U-shaped loop, said continuous tube further including third and fourth elongated legs extending generally parallel to the first and second elongated legs, said third and fourth legs being joined by a curved portion to form a second U-shaped loop, with the fourth leg having an end remote from the third leg which is connected to the outlet of the continuous tube, said first and second loops being joined by a lower curved section which extends diagonally between the first and second U-shaped loops;

a spiral rib means formed on the exterior of said continuous tube and extending substantially throughout the length of the continuous tube; and a resilient centrally located core having an elongated configuration which fits between the first and second U-shaped loops and includes a portion that extends between the first and second legs and a portion that extends between the third and fourth legs, said core being formed to resiliently engage the loops and said housing and further hold the loops in engagement with the housing in a manner such that the core and the housing, in cooperation with the continuous tube rib means, form spiral passages around each leg through which the blood must flow to reach the blood outlet.

12. The heat exchanger of claim 11 wherein said core has a U-shaped channel on one side which receives and conforms to said first loop, and a second U-shaped channel on another side of the core which receives and conforms to the second loop.

13. The heat exchanger of claim 12 wherein said housing includes surfaces having U-shaped channels for receiving said tube loops.

14. The heat exchanger of claim 11 wherein said blood inlet is located at an end of said first tube leg such that said blood flows directly into the spiral passages around said first leg.

15. A heat exchanger for a blood oxygenator comprising:

an elongated, vertically oriented housing having a blood inlet near one end of the housing:

an elongated heat exchange tube positioned in said housing having an inlet end near a second end of the housing and having an outlet end, said tube having a plurality of generally parallel tube legs extending in said housing including first leg having a first end and a second end, said leg extending from said first end adjacent said tube inlet end to said second end located directly in front of said housing blood inlet such that blood entering the housing through said blood inlet will first flow onto the exterior of said first leg second end before reaching the exterior of a second leg having an end connected to said first leg second end, and heat exchange rib means formed on the exterior of said tube; and means positioned in said housing cooperating with said rib means and said housing to form passages around said elongated tube legs through which the blood flows in heat exchange relation with the heat exchange fluid in said elongated tube while moving towards a blood outlet in said housing.

* * * * *